United States Patent [19]

Hirsch

[11] Patent Number: 4,762,836

[45] Date of Patent: Aug. 9, 1988

[54] AROMATASE INHIBITORS

[75] Inventor: Kenneth S. Hirsch, New Palestine, Ind.

[73] Assignee: Eli Lilly and Company, Indianapolis, Ind.

[21] Appl. No.: 560,282

[22] Filed: Dec. 12, 1983

Related U.S. Application Data

[63] Continuation-in-part of Ser. No. 463,086, Feb. 2, 1983, abandoned.

[51] Int. Cl.$^4$ ............................................ A61K 31/505
[52] U.S. Cl. .................................................. 514/256
[58] Field of Search ......................... 424/251; 514/256

[56] References Cited

U.S. PATENT DOCUMENTS

| 3,818,009 | 6/1974 | Taylor et al. | 260/25 R |
| 3,852,450 | 12/1974 | Silvestri et al. | 424/251 |
| 3,868,244 | 2/1975 | Taylor et al. | 71/76 |
| 3,869,456 | 3/1975 | Taylor et al. | 260/251 |
| 3,880,854 | 4/1975 | Campbell | 260/251 R |
| 3,887,708 | 6/1975 | Taylor et al. | 424/251 |

Primary Examiner—Allen J. Robinson
Attorney, Agent, or Firm—Robert A. Conrad; Leroy Whitaker

[57] ABSTRACT

This invention provides for a method of inhibiting aromatase and treating or preventing estrogen-dependent diseases in mammals by administering certain pyrimidine derivatives. Pharmaceutical formulations of the pyrimidine derivatives are also provided.

16 Claims, No Drawings

AROMATASE INHIBITORS

CROSS-REFERENCE

This application is a continuation-in-part of copending application Ser. No. 463,086, filed Feb. 2, 1983, now abandoned.

BACKGROUND OF THE INVENTION

Estrogens are synthesized from androgenic steroids. In the biosynthetic pathway for estrogen formation, aromatization is an essential step. It is generally believed that if the aromatase enzyme could be effectively inhibited, a useful treatment for estrogen dependent disorders could be obtained (see *Cancer Research*, Vol. 42, Suppl. 8:3261s (1982)).

Several estrogen dependent diseases exist which could be treated with aromatase inhibitors. These include breast cancer, endometriosis, polycystic ovarian disease, benign breast disease, and endometrial cancer. A beneficial effect of antiestrogens in the treatment of breast cancer has been well established (see *Br. J. Cancer*, 25, 270 (1971)). Two of the known aromatase inhibitors, testolactone and aminoglutethimide, have shown a beneficial effect in treatment of breast cancer. See *Cancer Research, supra*.

Endometriosis is characterized by an abnormal proliferation of the endometrium of the uterus. Since the endometrium is dependent on estradiol for its growth, an inhibitor of estrogen production should stop the progression of the disease.

Benign breast disease, or often called fibrocystic breast disease, appears to be dependent on ovarian steroids. See *Cancer*, 49, 2534 (1982). Aromatase inhibitors have not been tried in this disease, but antiestrogens seem to be of benefit. See *Obstet. Gynecol.*, 54, 80 (1979).

Polycystic ovarian disease is one of the most common causes of infertility in women. The disease appears to result from an abnormality in steroid metabolism, and the major form of therapy in this disease is the antiestrogen, clomiphene. See *Clin. Endocrinol.*, 12, 177 (1980).

It is the purpose of this invention to provide compounds which inhibit the enzyme aromatase in mammals and are therefore useful in the treatment or prevention of breast cancer and other estrogendependent diseases.

SUMMARY OF THE INVENTION

This invention provides for a method of inhibiting the enzyme aromatase in mammals with an effective amount of a compound of the formula I

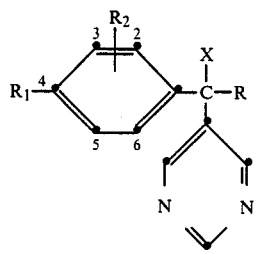

and pharmaceutically acceptable salts thereof, wherein R is

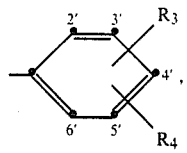

2-chloroethyl, $C_3$–$C_8$ cycloalkyl, phenoxy-substituted $C_1$–$C_4$ alkyl, or norbornan-2-yl;

$R_1$ is methyl, trifluoromethyl, methoxy, fluoro, chloro, bromo, or nitro;

$R_2$ is hydrogen, methyl, trifluoromethyl, methoxy, fluoro, chloro, bromo, or nitro;

each of $R_3$ and $R_4$ is independently hydrogen, methyl, methoxy, fluoro, or chloro; and X is hydrogen, hydroxy, methyl, or halo, with the proviso that if $R_1$ is methoxy, R must be substituted phenyl with at least one of $R_3$ and $R_4$ being other than hydrogen.

By virtue of their ability to inhibit the enzyme aromatase, the compounds of formula I are useful in the treatment and prevention of estrogen-dependent diseases, especially breast cancer, in mammals.

A further aspect of this invention is a pharmaceutical formulation comprising one or more of the compounds of formula I in combination with a suitable pharmaceutical carrier, diluent, or excipient therefor. The formulations provided by this invention are particularly useful in treating mammals suffering from estrogen-dependent diseases such as breast cancer.

DETAILED DESCRIPTION AND PREFERRED EMBODIMENT

The term "$C_1$–$C_4$ alkyl" refers to branched and straight chain aliphatic radicals of one to four carbon atoms such as methyl, ethyl, propyl, isopropyl, butyl, tert-butyl, and the like. The term "$C_3$–$C_8$ cycloalkyl" refers to the saturated alicyclic rings of three to eight carbon atoms such as cyclopropyl, methylcyclopropyl, cyclobutyl, cyclopentyl, cyclohexyl, cyclooctyl, and the like.

A preferred group of compounds useful in this invention are the compounds of formula I wherein:
(a) $R_1$ is fluoro or chloro,
(b) $R_2$ is hydrogen or chloro, especially at the 3-position,
(c) X is hydroxy, hydrogen, or fluoro, and
(d) R is phenyl ($R_3$ and $R_4$ are both hydrogen) or substituted phenyl, especially where one of $R_3$ and $R_4$ is chloro or fluoro, especially in the 4'-position.

Especially preferred compounds are those wherein X is hydrogen or hydroxy, and
(a) $R_1$ and $R_2$ are both chloro, especially where $R_2$ is at the 3-position, and R is unsubstituted phenyl, or
(b) $R_1$ is chloro or fluoro, $R_2$ is hydrogen, and R is mono-substituted phenyl, especially where one of $R_3$ and $R_4$ is chloro or fluoro, preferably at the 4'-position, and the other of $R_3$ and $R_4$ is hydrogen.

The most preferred compound is 5-bis(4-chlorophenyl)methylpyrimidine and its pharmaceutically acceptable salts.

A preferred method of treatment according to this invention comprises administering a dose effective for inhibiting the enzyme aromatase of one of the preferred compounds of this invention. Similarly, a preferred formulation according to this invention comprises one of the preferred compounds of this invention in combination with a pharmaceutical carrier therefor.

Most of the compounds used in this invention and methods of making the compounds are disclosed in U.S. Pat. No. 3,818,009. A preferred and novel method of preparing the pyrimidinemethanols in this invention (I, X is hydroxy) is taught in U.S. Pat. No. 3,869,456. Both patents are expressly incorporated in this application by reference. The compounds as disclosed in the patents are described as being useful as fungicides, bactericides, herbicides, and plant growth regulators. The methods of using the compounds of Formula I as fungicides and as plant growth regulators are claimed in U.S. Pat. Nos. 3,887,708 and 3,868,244, respectively. The patents do not disclose any utility for use in humans or any utility related to the inhibition of aromatase. The compounds used in this invention wherein X is methyl are claimed in U.S. Pat. No. 3,818,009 and can be prepared from the corresponding compounds where X is hydrogen by alkylation with a methyl halide following the general liquid ammonia/alkali metal amide procedure as described in U.S. Pat. No. 2,727,895.

The compounds of Formula I wherein R is 2-chloroethyl can be prepared from the corresponding vinyl compounds taught in the above patents by any of a number of methods known in the art such as the addition of hydrogen chloride under anti-Markovnikov conditions. Alternatively, the 2-chloroethyl compounds may be prepared in the same manner as taught in the above references utilizing the appropriate $\beta$-chloropropiophenone derivative.

As will be recognized by those skilled in the art, except when R is a phenyl group substituted identically to the substitution of $R_1$ and $R_2$, the compounds of Formula I contain an asymmetric carbon atom. This invention is not limited to any particular isomer but includes the individual enantiomers as well as the racemates of the compounds of Formula I.

The pharmaceutically acceptable acid addition salts of the bases represented by Formula I can be prepared employing those acids of sufficient acidity to form acid addition salts with the weakly basic pyrimidine group. These include both inorganic and organic acids such as hydrochloric, hydrobromic, hydriodic, sulfuric, phosphoric, oxalic, methanesulfonic, benzenesulfonic, p-toluenesulfonic, maleic, and the like acids. Preferred acids for salt formation are the inorganic acids, especially hydrochloric acid.

The compounds may be administered by any number of routes, including the oral, subcutaneous, intramuscular, intravenous, transdermal, and rectal routes, usually employed in the form of a pharmaceutical composition. Such compositions are prepared in a manner well known in the pharmaceutical art and comprise at least one active compound.

Accordingly, the invention includes a pharmaceutical composition comprising as active ingredient a compound of formula I associated with a pharmaceutically acceptable carrier. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semi-solid or liquid material which acts as a vehicle, excipient or medium for the active ingredient. Thus, the composition can be in the form of tablets, pills, powders, lozenges, sachets, cachets, elixirs, emulsions, solutions, syrups, suspensions, aerosols (as a solid or in a liquid medium), ointments containing for example up to 10% by weight of the active compound, soft and hard gelatin capsules, suppositories, sterile injectable solutions, and sterile packaged powders.

Some examples of suitable carriers are lactose, dextrose, sucrose, sorbitol, mannitol, starches, gum acacia, calcium phosphate, alginates, calcium silicate, microcrystalline cellulose, polyvinylpyrrolidone, cellulose, tragacanth, gelatin, syrup, methyl cellulose, methyl- and propylhydroxybenzoates, talc, magnesium stearate, water, or mineral oil. The formulations can additionally include lubricating agents, agents, emulsifying and suspending agents, preserving agents, sweetening agents or flavoring agents. The compositions of the invention may, as is well known in the art, be formulated so as to provide quick, sustained, or delayed release of the active ingredient after administration to the patient.

For oral administration, a compound of this invention is admixed with carriers and diluents molded into tablets or enclosed in gelatin capsules. The mixtures can alternatively be dissolved in liquids such as ten percent aqueous glucose solution, isotonic saline, sterile water, or the like, and administered intravenously or by injection. Such solutions can, if desired, be lyophilized and stored in a sterile ampoule ready for reconstitution by the addition of sterile water for ready intramuscular injection.

Preferably the compositions are formulated in a unit dosage form, each dosage containing from about 1 to 500 mg.; more usually about 5 to 300 mg., of the active ingredient. The term "unit dosage form" refers to physically discrete units suitable as unitary dosages for human subjects and other mammals, each unit containing a predetermined quantity of active material calculated to produce the desired therapeutic effect, in association with the required pharmaceutical carrier.

The active compounds are effective over a wide dosage range. For example, dosages per day will normally fall within the range of about 0.05 to 300 mg./kg. In the treatment of adult humans, the range of about 0.1 to 50 mg./kg., in single or divided doses, is preferred. However, it will be understood that the amount of the compound actually administered will be determined by a physician, in the light of the relevant circumstances including the condition to be treated, the choice of compound to be administered, the age, weight, and response of the individual patient, the severity of the patient's symptoms, and the chosen route of administration, and therefore the above dosage ranges are not intended to limit the scope of the invention in any way.

The compounds used in this invention are useful in preventing or therapeutically treating estrogen-dependent diseases, including breast cancer, in mammals by virtue of their ability to inhibit the enzyme aromatase. The ability to inhibit aromatase was demonstrated by employing a modification of the isolated rat ovarian microsome method of Brodie et al. in *J. Steroid Biochem.*, 7, 787 (1976). In this test system, ovarian microsomes are obtained from rats treated with pregnant mares serum gonadotropin. Test compounds are added to reaction vials containing 0.1 $\mu$M 4-androstene-3,17-dione, 100,000 dpm 1,2[$^3$H]-androstenedione, the microsomes and a NADPH generating system. The concentrations of the inhibitors tested ranged between 0.005 and 10 $\mu$M. In this assay, aromatization of androstenedione results in the production of [$^3$H]-H$_2$O which is isolated by extracting the samples with chloroform and treating the aqueous phase with charcoal to remove the free steroid. Samples are counted in a liquid scintillation spectrometer and the percent inhibition determined by comparing the results with the samples incubated without inhibitor. Potency is determined based on the concentration of inhibitor in μM required to produce a 50% inhibition of enzyme activity (EC$_{50}$) when the concentration of substrate (androstenedione) is 0.1 μM. The EC$_{50}$'s of certain of the compounds of formula I are summarized in Table 1.

TABLE 1

Aromatase Inhibition in the Rat Ovarian Microsome Assay

| Compound of Formula I | EC$_{50}$* |
|---|---|
| α-cyclohexyl-α-(4-methylphenyl)-5-pyrimidinemethanol | 6.4 |
| α-(3-chlorophenyl)-α-(4-chlorophenyl)-5-pyrimidinemethanol | 0.35 |
| α-(4-trifluoromethylphenyl)-α-phenyl-5-pyrimidinemethanol | 1.95 |
| α-(4-methoxy-3-methylphenyl)-α-(3,4-dimethylphenyl)-5-pyrimidinemethanol | 1.4 |
| α-(2-chlorophenyl)-α-(4-chlorophenyl)-5-pyrimidinemethanol | 4.1 |
| α-(2-chloro-4-methoxyphenyl)-α-(4-chlorophenyl)-5-pyrimidinemethanol | 4.3 |
| α-(4-chlorophenyl)-α-(norbornan-2-yl)-5-pyrimidinemethanol | 7.8 |
| α-(4-chlorophenyl)-α-(4-fluorophenyl)-5-pyrimidinemethanol | 0.18 |
| α-(4-methoxyphenyl)-α-(2-chlorophenyl)-5-pyrimidinemethanol | ** |
| α-(2-chloroethyl)-α-(4-fluorophenyl)-5-pyrimidinemethanol | 1.8 |
| α-phenyl-α-(3,4-dimethylphenyl)-5-pyrimidinemethanol | 3.2 |
| 5-[(2-chlorophenyl)fluoro-(4-fluorophenyl)methyl]pyrimidine | 1.2 |
| 5-[(2-chlorophenyl)(4-chlorophenyl)methyl]pyrimidine | 0.5 |
| α-(3-chlorophenyl)-α-(4-methoxyphenyl)-5-pyrimidinemethanol | 4.1 |
| α-cyclopropyl-α-(4-fluorophenyl)-5-pyrimidinemethanol | 4.2 |
| α-(4-chlorophenyl)-α-(4-phenoxy-n-butyl)-5-pyrimidinemethanol | 5.4 |
| α-(2-chlorophenyl)-α-(4-fluoro-2-methoxyphenyl)-5-pyrimidinemethanol | 5.6 |
| α-(3,4-dichlorophenyl)-α-phenyl-5-pyrimidinemethanol | 1.0 |
| α-(4-methoxy-3-methylphenyl)-α-(3-methylphenyl)-5-pyrimidinemethanol | 8.3 |
| α-(4-chlorophenyl)-α-(3-fluorophenyl)-5-pyrimidinemethanol | 1.65 |
| 5-[(3,4-dichlorophenyl)fluorophenylmethyl]pyrimidine | 1.35 |

TABLE 1-continued

Aromatase Inhibition in the Rat Ovarian Microsome Assay

| Compound of Formula I | EC$_{50}$* |
|---|---|
| α-(2,4-dichlorophenyl)-α-phenyl-5-pyrimidinemethanol | 8.0 |
| α-(4-nitrophenyl)-α-phenyl-5-pyrimidinemethanol | 0.27 |
| α-cyclohexyl-α-(2,4-dichlorophenyl)-5-pyrimidinemethanol | 13.8 |
| α-(3-chlorophenyl)-α-(4-fluorophenyl)-5-pyrimidinemethanol | 1.2 |
| α-(4-fluorophenyl)-α-phenyl-5-pyrimidinemethanol | 2.2 |
| 5-bis(4-chlorophenyl)methylpyrimidine | 0.055 |
| 5-[(3-chlorophenyl)(4-chlorophenyl)fluoromethyl]pyrimidine | 0.68 |
| α,α-bis(4-chlorophenyl)-5-pyrimidinemethanol | 0.071 |
| α-(2,4-dimethylphenyl)-α-phenyl-5-pyrimidinemethanol | 3.5 |
| α,α-bis(4-methylphenyl)-5-pyrimidinemethanol | 0.41 |
| α-(4-chloro-2-methoxyphenyl)-α-phenyl-5-pyrimidinemethanol | 3.6 |
| α-(4-chlorophenyl)-α-cyclohexyl-5-pyrimidinemethanol | 4.0 |
| α-(2-chlorophenyl)-α-(4-fluorophenyl)-5-pyrimidinemethanol | 4.1 |
| α-(4-bromophenyl)-α-cyclopropyl-5-pyrimidinemethanol | 5.4 |
| α-(2,4-difluorophenyl)-α-phenyl-5-pyrimidinemethanol | 5.6 |
| α-(4-chlorophenyl)-α-cyclopropyl-5-pyrimidinemethanol | 5.7 |
| α-(4-fluorophenyl)-α-(3-methoxyphenyl)-5-pyrimidinemethanol | 1.25 |
| 5-[(4-chlorophenyl)fluoro(4-fluorophenyl)methyl]pyrimidine | 0.195 |
| 5-[bis(4-chlorophenyl)fluoromethyl]pyrimidine | 0.078 |
| 5-[1,1-bis(4-chlorophenyl)ethyl]pyrimidine | 0.082 |
| α,α-bis(4-fluorophenyl)-5-pyrimidinemethanol | 0.33 |
| α-(3-fluorophenyl)-α-(4-fluorophenyl)-5-pyrimidinemethanol | 1.15 |

*Concentration of compound in μM required to achieve 50% inhibition of aromatase activity when substrate concentration is 0.1 μM.
**17.6% inhibition at 10.0 μM.

By virtue of their ability to inhibit the enzyme aromatase, the compounds of this invention are able to inhibit the synthesis of estrogens in mammals, thereby making the compounds useful in the treatment of estrogen-dependent diseases, such as breast cancer. This *in vivo* activity was demonstrated in the following test systems.

Estrogen Synthesis Inhibition in Rats

Immature female Wistar rats (45–55 grams) were divided into control and test groups of 2–8 animals each. Test compounds were administered for seven days either daily by gavage in corn oil or as a component of the diet. Control animals received either corn oil or diet without the test compound. Beginning on the fourth day of the test, all animals treated with the test compound and one half of the control animals were given a subcutaneous injection of 1.0 mg. of testosterone propionate in corn oil. The remaining control animals received only an equivalent volume of corn oil. On the seventh day of the test, rats treated with testosterone propionate were injected subcutaneously with 100 μCi of [$^3$H]-testosterone in 50 μl. of saline-ethanol (3:1).

After two hours, the animals were killed by decapitation. Uteri were isolated, trimmed of extraneous connective tissue, and weighed. As summarized in Table 2 below, the corn oil treated animals exhibited low uterine weight and represent unstimulated or negative controls. In the control animals treated with testosterone propionate, estrogens produced by aromatization stimulated the uterus resulting in an increase in weight. Compounds which inhibit aromatization produced uterine weights significantly lower than those of the testosterone treated controls.

Ovaries from rats treated with [$^3$H]-testosterone were excised, cleaned of extraneous tissue, and homogenized in 2.5 ml. of a 1.0 mM potassium phosphate buffer containing 3.0 mM MgCl$_2$.6H$_2$O, 320 mM sucrose, and 0.25% Triton X-100 (polyethylene glycol p-isooctyl phenyl ether, Rohm and Haas) at pH 6.5. The ovarian steroids were extracted with 1.5 ml. of 9:1 toluene/ethanol to which had been added 25 to 100 mcg. each of unlabelled estradiol, estriol, and estrone, and approximately 1000 dpm of [$^{14}$C]-estradiol. The samples were vortexed, centrifuged at 500×g for 10 minutes, and the organic phase was transferred to a conical vial. Two additional extractions were performed on the residue in the same way. The pooled organic extracts were evaporated for subsequent thin-layer chromatography Ovarian proteins were precipitated by the addition of 5.0 ml. of ethanol to the remaining aqueous phase. After an overnight incubation at 4° C., the samples were centrifuged at 1500×g for 10 minutes. The supernatant was discarded and the pellet was dissolved in 0.3 N potassium hydroxide. Protein was determined according to the method of Bradford, *Analytical Biochemistry*, 72, 248 (1976).

The organic residue from each above extraction was redissolved in 9:1 dichloromethane/methanol. The solution of each sample was applied to separate silica gel thin layer chromatography plates which contained a fluorescent indicator. The plates were developed the first dimension with 160:38:1.5:0.5 dichloromethane/ethyl acetate/methanol/acetic acid to within 3 cm. of the top of the plate. After air-drying, the plate was developed in the second dimension with 180:19:1 dichloromethane/methanol/ammonium hydroxide. The plate was air-dried and viewed under 254 nm. UV light.

The visible spots were marked and the plates were sprayed with primulin (0.001% in 4:1 acetone/water) according to the method of Wright, *J. Chromatography,* 59, 220 (1971) which allowed for the identification of additional steroids under 365 nm. UV light. The spots were scraped from the plate using a glass wool plugged Pasteur pipet attached to a vacuum line. The steroids were eluted directly into scintillation vials by the addition of 0.2 ml. of dichloromethane followed by two washes each of 2.0 ml. of methanol. The organic solvent was evaporated and 10.0 ml. of scintillation fluid (Beckman Ready Solv-NA) was added to the vials. Samples were analyzed by liquid scintillation spectrometry and the corrections were made based on the recoveries of the [$^{14}$C]-steroid. Steroid concentrations are expressed as femtomoles per milligram protein.

TABLE 2

Effects of Compounds of Formula I on estrogen levels and uterine weight

| Test No. | Compound | Dose* | Animals | Mean Uterine Weight (mg.) | Mean Steroid Concentration** | | |
|---|---|---|---|---|---|---|---|
| | | | | | estradiol | estrone | estriol |
| I | α,α-bis(4-chlorophenyl)- | 30 | 3 | 130.67 | 0.31+ | 0.34 | 1.24 |
| | 5-pyrimidinemethanol | 300 | 2 | 75.00+ | 0.14+ | 0.70 | 2.74 |
| | testosterone-treated control | — | 6 | 176.67 | 2.07 | 0.64 | 1.98 |
| | Corn oil control | — | 4 | 51.75+ | — | — | — |
| II | 5-bis(4-chlorophenyl)- | 30 | 4 | 92.25+ | 0.14+ | 0.14 | 0.59 |
| | methylpyrimidine | 300 | 5 | 80.20+ | 0.15+ | 0.12 | 0.29 |
| | Testosterone-treated control | — | 8 | 179.13 | 0.97 | 0.20 | 0.36 |
| | Corn oil control | — | 5 | 79.80+ | — | — | — |

*ppm in feed. 300 ppm corresponds to approximately 30 mg./kg./day; 30 ppm corresponds to approximately 3 mg./kg./day.
**femtomoles per milligram of protein.
+significantly different from testosterone-treated control, $p < 0.05$.

DMBA-induced Mammary Tumor Inhibition

Mammary tumors were produced in female Sprague-Dawley rats which were 50–60 days old by the gavage administration of 20 mg. of 7,12-dimethylbenz[a]anthracene (DMBA). About six weeks after DMBA administration, the mammary glands were palpated at weekly intervals for the appearance of tumors. Whenever one or more tumors appeared and were measurable in an animal, that animal was selected for experimentation. An attempt was made to uniformly distribute the various sizes of tumors in the treated and control groups such that one group did not start with rats having tumors which, on the average, were significantly larger than those of any other group. Each control and test group contained 8 animals. The test compound was administered either mixed into the food at a concentration of 300 ppm (corresponding to an appropriate daily dose of 30 mg./kg.) or the compounds were dissolved or suspended in corn oil and administered once daily by gavage. Every experiment included a group of control rats having tumors and were either given food without the compound admixed or corn oil vehicle by gavage, depending on how the test compound was administered. The tumors were measured at the start of the experiments and generally had an area of approximately 15–100 mm$^2$. The area of each tumor was calculated by multiplying the shortest and longest diameters of the tumor. The treatment and measurement of animals continued for 4–8 weeks at which time the final areas of the tumors were determined. For each compound (and control) at each dose level, the change in the mean tumor area was determined. The mean change was analyzed for its significance using Dunnett's t-test. The results of these tests are shown in Table 3 below.

TABLE 3

Anti-Tumor Activity

| Test No. | Compound | Dose* | Duration of Test | Mean Tumor Area (mm$^2$) Start | Finish |
|---|---|---|---|---|---|
| I | Control | — | 5 weeks | 72.2 | 924.3 |
|  | α,α-bis(4-chlorophenyl)-5-pyrimidinemethanol | 300 ppm |  | 60.7 | 10.0+ |
| II | Control | — | 5 weeks | 48.4 | 1116 |
|  | 5-bis(4-chlorophenyl)-methylpyrimidine | 300 ppm |  | 78.6 | 154 |
| III | Control | — | 8 weeks | 144.5 | 1371 |
|  | α,α-bis(4-chlorophenyl)-5-pyrimidinemethanol | 300 ppm |  | 160.4 | 355+ |
| IV | Control | — | 4 weeks | 54.8 | 913.6 |
|  | α,α-bis(4-chlorophenyl)-5-pyrimidinemethanol | 5 mg./kg. |  | 56.3 | 123.5 |
|  |  | 30 mg./kg. |  | 71.5 | 34.3 |
| V | Control | — | 5 weeks | 59 | 1381 |
|  | 5-bis(4-chlorophenyl)-methylpyrimidine | 1 mg./kg. |  | 66 | 210+ |
|  |  | 7.5 mg./kg. |  | 63 | 159+ |
|  |  | 15 mg./kg. |  | 50 | 9+ |
|  |  | 30 mg./kg. |  | 69 | 146+ |

*when dosed in the diet, reported as ppm. 300 ppm corresponds to approximately 30 mg./kg./day. Doses reported in mg./kg. given daily by gavage.
+statistically different from control, $p < 0.05$.

In order to more fully illustrate the operation of this invention, the following formulation examples are provided. The examples are illustrative only and are not intended to limit the scope of the invention. The formulations employ as active compounds any of the pharmaceutical compounds of formula I.

EXAMPLE 1

Hard gelatin capsules are prepared using the following ingredients:

|  | per capsule |
|---|---|
| Active compound | 250 mg. |
| Starch dried | 200 mg. |
| Magnesium stearate | 10 mg. |
| Total | 460 mg. |

The above ingredients are mixed and filled into hard gelatin capsules in 460 mg. quantities.

EXAMPLE 2

Capsules each containing 20 mg. of medicament are made as follows:

|  | per capsule |
|---|---|
| Active ingredient | 20 mg. |
| Starch | 89 mg. |
| Microcrystalline cellulose | 89 mg. |
| Magnesium stearate | 2 mg. |
| Total | 200 mg. |

The active ingredient, cellulose, starch and magnesium stearate are blended, passed through a No. 45 mesh U.S. sieve and filled into hard gelatin capsules in 200 mg. quantities.

EXAMPLE 3

Capsules each containing 100 mg. of active ingredient are made as follows:

|  | per capsule |
|---|---|
| Active ingredient | 100 mg. |
| Polyoxyethylenesorbitan monooleate | 50 mcg. |
| Starch powder | 250 mg. |

The above ingredients are thoroughly mixed and are placed in an empty gelatin capsule.

EXAMPLE 4

Tablets each containing 10 mg. of active ingredient are made up as follows:

|  | per tablet |
|---|---|
| Active ingredient | 10 mg. |
| Starch | 45 mg. |
| Microcrystalline cellulose | 35 mg. |
| Polyvinylpyrrolidone (as 10% solution in water) | 4 mg. |
| Sodium carboxymethyl starch | 4.5 mg. |
| Magnesium stearate | 0.5 mg. |
| Talc | 1 mg. |
| Total | 100 mg. |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°-60° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

EXAMPLE 5

A tablet formula is prepared using the ingredients below:

|  | per tablet |
|---|---|
| Active compound | 250 mg. |
| Cellulose microcrystalline | 400 mg. |
| Silicon dioxide fumed | 10 mg. |
| Stearic acid | 5 mg. |

-continued

|  | per tablet |
|---|---|
| Total | 665 mg. |

The components are blended and compressed to form tablets each weighing 665 mg.

EXAMPLE 6

Suppositories each containing 25 mg. of active ingredient are made as follows:

|  | per suppository |
|---|---|
| Active ingredient | 25 mg. |
| Saturated fatty acid glycerides to | 2,000 mg. |

The active ingredient is passed through a No. 60 mesh U.S. sieve and suspended in the saturated fatty acid glycerides previously melted using the minimum heat necessary. The mixture is then poured into a suppository mold of nominal 2 g. capacity and allowed to cool.

EXAMPLE 7

Suspensions each containing 5 mg. of medicament per 5 ml. dose are made as follows:

|  | per 5 ml. of suspension |
|---|---|
| Active ingredient | 5 mg. |
| Sodium carboxymethyl cellulose | 50 mg. |
| Syrup | 1.25 ml. |
| Benzoic acid solution | 0.10 ml. |
| Flavor | q.v. |
| Color | q.v. |
| Purified water to | 5 ml. |

The medicament is passed through a No. 45 mesh U.S. sieve and mixed with the sodium carboxymethylcellulose and syrup to form a smooth paste. The benzoic acid solution, flavor and color is diluted with some of the water and added, with stirring. Sufficient water is then added to produce the required volume.

EXAMPLE 8

An aerosol solution is prepared containing the following components:

|  | Weight % |
|---|---|
| Active ingredient | 0.25 |
| Ethanol | 29.75 |
| Propellant 22 (Chlorodifluoromethane) | 70 |

The active compound is mixed with ethanol and the mixture added to a portion of the propellant 22, cooled to −30° C. and transferred to a filling device. The required amount is then fed to a stainless steel container and diluted further with the remaining amount of propellant. The valve units are then fitted to the container.

I claim:

1. The method of inhibiting aromatase in a mammal which comprises administering to said mammal an aromatase inhibiting dose of a compound of formula I

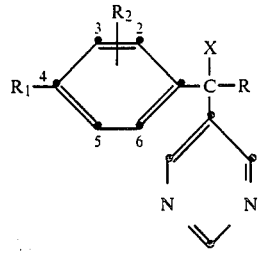

and pharmaceutically acceptable salts thereof, wherein R is

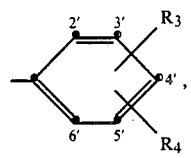

2-chloroethyl, $C_3$–$C_8$ cycloalkyl, phenoxy-substituted $C_1$–$C_4$ alkyl, or norbornan-2-yl, $R_1$ is methyl, trifluoromethyl, methoxy, fluoro, chloro, bromo, or nitro;

$R_2$ is hydrogen, methyl, trifluoromethyl, methoxy, fluoro, chloro, bromo, or nitro;

each of $R_3$ and $R_4$ is independently hydrogen, methyl, methoxy, fluoro, or chloro; and X is hydrogen, hydroxy, methyl, or halo, with the proviso that if $R_1$ is methoxy, R must be substituted phenyl with at least one of $R_3$ and $R_4$ being other than hydrogen.

2. A method according to claim 1 wherein R is

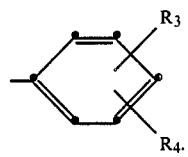

3. The method according to claim 2 wherein $R_1$ is chloro or fluoro.

4. The method according to claim 3 wherein one of $R_3$ and $R_4$ is chloro or fluoro in the 4'-position and $R_2$ and the other of $R_3$ and $R_4$ are both hydrogen.

5. The method according to claim 4 wherein X is hydrogen.

6. The method according to claim 4 wherein X is hydroxy.

7. The method according to claim 5 wherein the compound is 5-bis(4-chlorophenyl)methylpyrimidine or a pharmaceutically acceptable salt thereof.

8. The method of preventing or treating estrogen-dependent diseases in a mammal which comprises administering an effective amount of a compound according to the formula

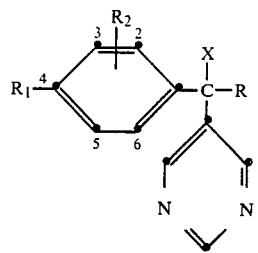

pharmaceutically acceptable salts thereof, wherein R is

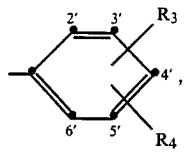

2-chloroethyl, $c_3$–$C_8$ cycloalkyl, phenoxy-substituted $C_1$–$C_4$ alkyl, or norbornan-2-yl, $R_1$ is methyl, trifluoromethyl, methoxy, fluoro, chloro, bromo, or nitro;

$R_2$ is hydrogen, methyl, trifluoromethyl, methoxy, fluoro, chloro, bromo, or nitro;

each of $R_3$ and $R_4$ is independently hydrogen, methyl, methoxy, fluoro, or chloro; and X is hydrogen, hydroxy, methyl, or halo, with the proviso that if $R_1$ is methoxy, R must be substituted phenyl with at least one of $R_3$ and $R_4$ being other than hydrogen, to said mammal.

9. The method according to claim 8 wherein R is

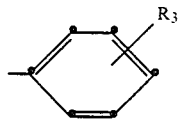

$R_2$ is hydrogen.

10. The method according to claim 9 wherein $R_1$ and $R_3$ are each independently chloro or fluoro and $R_3$ is in the 4'-position.

11. The method according to claim 10 wherein X is hydrogen, hydroxy, or fluoro.

12. The method according to claim 11 wherein the compound is 5-bis(4-chlorophenyl)methylpyrimidine or a pharmaceutically acceptable salt thereof.

13. The method according to claim 8 wherein the estrogen-dependent disease is breast carcinoma.

14. The method according to claim 13 wherein R is

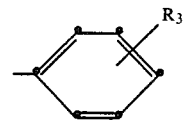

and $R_2$ is hydrogen.

15. The method according to claim 14 wherein $R_1$ and $R_3$ are each independently chloro or fluoro and $R_3$ is in the 4'-position.

16. The method according to claim 15 wherein the compound is 5-bis(4-chlorophenyl)methylpyrimidine or a pharmaceutically acceptable salt thereof.

* * * * *

UNITED STATES PATENT AND TRADEMARK OFFICE
CERTIFICATE OF CORRECTION

PATENT NO. : 4,762,836

DATED : August 9, 1988

INVENTOR(S) : Kenneth S. Hirsch

It is certified that error appears in the above-identified patent and that said Letters Patent is hereby corrected as shown below:

On the title page, column 1,

"Inventor: Kenneth S. Hirsch, New Palestine, Ind."

should read

--Inventors: Kenneth S. Hirsch, New Palestine, Harold M. Taylor, Indianapolis, both of Ind. --.

In column 11, line 65, "I claim:" should read --We claim:--.

Signed and Sealed this

Fourteenth Day of March, 1989

Attest:

DONALD J. QUIGG

*Attesting Officer*  *Commissioner of Patents and Trademarks*